United States Patent [19]

Seare, Jr.

[11] Patent Number: 4,798,195

[45] Date of Patent: Jan. 17, 1989

[54] MOLDABLE RETRACTOR FOR USE IN SURGERY

[76] Inventor: William J. Seare, Jr., 1321 Harvard Ave., Salt Lake City, Utah 84105

[21] Appl. No.: 928,539

[22] Filed: Nov. 7, 1986

[51] Int. Cl.$^4$ .............................................. A61B 17/02
[52] U.S. Cl. ........................................ 128/20; 128/19
[58] Field of Search .................. 128/3, 12, 17, 18, 19, 128/20, 85, 87 R, 87 A, 89 R; 269/328, 322

[56] References Cited

U.S. PATENT DOCUMENTS

| | | | |
|---|---|---|---|
| 3,761,301 | 10/1973 | Tupper | 128/20 |
| 4,082,257 | 4/1978 | Strickland | 269/328 |
| 4,204,533 | 5/1980 | Forster et al. | 128/133 |
| 4,274,398 | 6/1981 | Scott, Jr. | 128/20 |
| 4,421,107 | 12/1983 | Estes et al. | 128/20 |
| 4,434,791 | 3/1984 | Darnell | 128/20 |
| 4,549,537 | 10/1985 | Ender | 128/89 R |
| 4,610,243 | 9/1986 | Ray | 128/20 |
| 4,616,633 | 10/1986 | Garcia | 128/20 |
| 4,627,421 | 12/1986 | Symbas et al. | 128/20 |

FOREIGN PATENT DOCUMENTS 2437863  2/1975  Fed. Rep. of Germany ........ 128/20

OTHER PUBLICATIONS

Microtek Medical, Inc., "Surgical Retractor Stay System".
ASII, "Hand Surgery".
Microtek Medical Inc., "Hands Off!".
"Porex TM Retractor Table".

Primary Examiner—Barry S. Richman
Assistant Examiner—T. J. Wallen
Attorney, Agent, or Firm—Workman, Nydegger & Jensen

[57] ABSTRACT

A moldable, weighted, surgical retractor and methods for its use. The surgical retractor comprises a generally flat plate having a plurality of protrusions or arms extending outwardly from the interior body of the plate. Included around the periphery of the plate and the arms are a plurality of slots. The slots may be of any size and shape and function to hold surgical stays in place during the surgical procedure. The arms or protrusions of the present invention may be placed in a variety of positions so that stays may hold certain portions of the surgical site in any desired direction. For example, arms or protrusions of the present invention may be lifted upwardly and stays may be connected to the upwardly extending arms. As a result, upward lifting forces may be directed into the surgical site to hold blood vessels, tendons, bones or other structural features upward within the surgical area. In addition, the arms of the retractor may be molded around a portion of the patient's anatomy in order to hold it in place. The present invention is also directed to a system which includes the retractor of the present invention along with surgical stays of varying elastic properties and diameters. As a result, the force which the stays exert on a surgical area can be finely adjusted and chosen as desired by the surgeon.

25 Claims, 2 Drawing Sheets

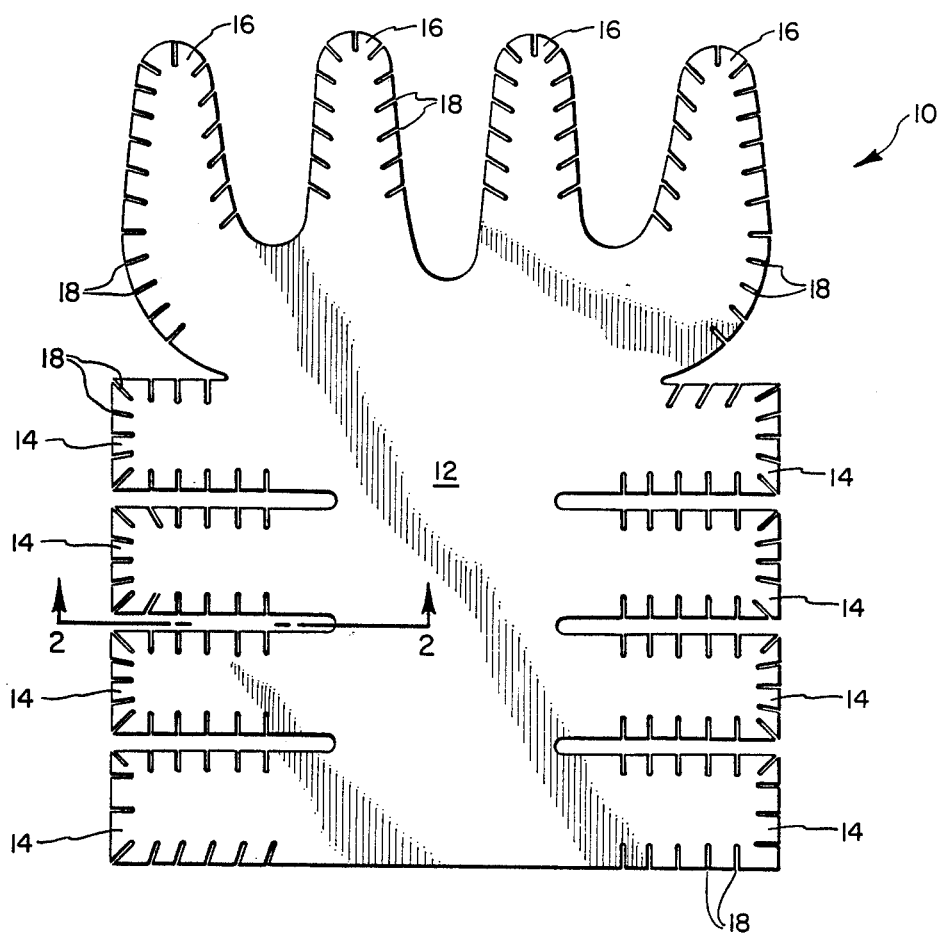
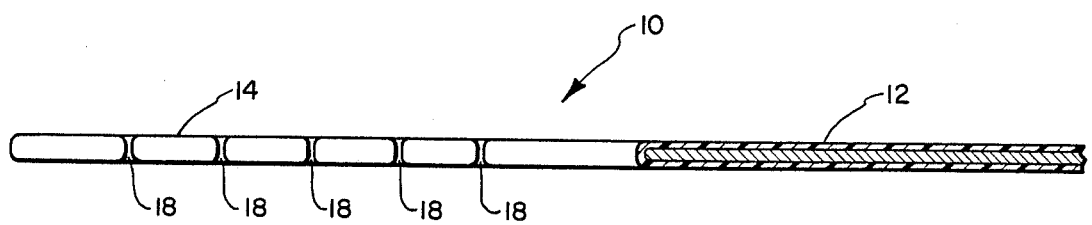
FIG. 1
FIG. 2

MOLDABLE RETRACTOR FOR USE IN SURGERY

BACKGROUND

1. Field of the Invention

The present invention generally relates to retractors for use in surgery. More particularly, the present invention relates to a moldable retractor particularly adaptable for use in surgery on the extremities, such as the hand.

2. Background of the Invention

In order to perform various surgical procedures it is, of course, necessary to immobilize the area on which the surgery is being performed. In addition, it is necessary and desirable to hold certain tissues out of the vicinity in which the surgeon is working and away from the actual surgical site or to hold sutures or other delicate tissues in certain locations in space. These two interrelated problems of immobilizing certain parts of the body and retracting certain tissues in a particular manner have spawned the development of a variety of devices which are generally referred to as retractors.

In order to perform surgery on a particular part of a patient's body, it is necessary to hold that body part in a stationary position. This allows the surgeon to proceed with the operation in a controlled and efficient manner. The degree of difficulty encountered in immobilizing particular parts of the body may vary widely.

In particular, the problem of immobilizing the subject area is increased when surgery is performed on the extremities such as the arms, legs, hands, feet, and the head and neck which are easily moved by the patient and which may also be moved by relatively small external forces. In addition, because of the relatively small mass of the extremity, as compared to the larger mass of the remainder of the body, the extremities are particularly difficult to immobilize.

An additional problem encountered in performing surgery on the extremities, particularly the hands, feet, head and neck is that delicate and complex surgical procedures are often required as a direct result of the extremely high concentration of bones, nerves, blood vessels, tendons and other similar structures contained within the hands, feet, head and neck. It will be appreciated that the high concentration of structural features encountered in the extremities is a result of the plurality of the complex and delicate movements performed by the hands and feet.

Because of the high concentration of delicate structural features contained within the extremities, it is difficult to perform surgery on the hand or feet. For example, it may be necessary to move nerves and blood vessels out of the surgical area so that tendons or other structures can be repaired. During such a procedure, it is extremely easy to damage the nerves and blood vessels, as well as the tendons. The moving of nerves, blood vessels, and tendons within or away from the surgical area and subsequently holding them in the desired location may be a critical step in the surgical procedure.

It can be seen, therefore, that the dual problems of immobilizing an extremity, and moving delicate structures within or away from the surgical site makes surgery on the extremities tedious and difficult.

In order to aid the surgeon in the performance of this difficult and delicate surgery, various types of "retractors" have been developed. Such retractors are often comprised of a simple annular or circular frame. The frame may be, for example, molded such that it will fit over the particular portion of the body which is the subject of the surgical procedure.

The annular or circular frame conventionally includes means for attaching various "stays" or other types of members to the frame. These stays may, in turn, be used for the purpose of holding various organs or tissue structures away from the surgical area, holding such tissues at desired locations within the surgical area, or they may be used in order to hold the incision open so that the surgeon may perform the surgical procedure without being hindered by closure of the incision.

There are several variations of the type of retractor described above. In one embodiment of such a retractor, it is possible to interchange certain parts of the circumference of the retractor with a section of retractor having a particular specialized shape. This allows the surgeon to modify, somewhat, the exact shape of the circumference of the retractor and provides for use of the retractor in a wider variety of surgical procedures.

As mentioned above, the demands of extremity surgery are unique because of the difficulty in immobilizing the extremity and also the difficulty which is encountered in performing surgical procedures in and around the high concentration of nerves, tendons, blood vessels, bones, and other such structures which are contained within the hand. The retractors described above, which consist simply of an annular or circular frame, have been found to be inadequate for use in hand surgery and other similar procedures because of their lack of flexibility and adjustability in three dimensions in space.

As a result, several attempts have been made to develop retractors which are particularly adaptable for use in extremity surgery. One such retractor comprises a flat sheet of material which is cut into the general outline of a hand. Using this device, the fingers may be strapped to the finger-shaped extensions of the retractor board. This type of retractor has been found to be somewhat useful in helping to solve the problems of immobilizing the hand; however, it is not particularly adaptable for aiding in the actual surgical procedure. That is, it is not adaptable for keeping an incision open or in holding nerves, blood vessels, tendons, and the like in a desired location in three-dimensional space.

Another retractor which is commonly used in hand surgery comprises a paddle-shaped pallet. The paddle-shaped pallet is sufficiently large that a hand may be laid on the pallet without having the fingers extend over the edge of the pallet. The pallet includes a series of notches around its periphery. This allows metal "ball and link" chains to be hooked within the various notches in the desired position. The ball and link chains are then used to hold the surgical incision open or to hold blood vessels, bones, tendons, and the like in a desired position. Furthermore, the pallet may be provided with slots in which straps may be inserted to hold the fingers and wrist in place. This type of hand retractor has seen fairly wide acceptance in the surgical market.

The paddle-shaped pallet hand retractor, however, has several serious limitations. One limitation is that the retractor is not sufficiently weighted to fully immobilize the hand. As a result, relatively small external forces, such as bumping into the hand, will cause the surgical site to move out of place. In addition, it is not possible to move the fingers or the various tissues encountered in the surgical procedure in a three-dimensional manner.

That is, it is only possible to hold the hand in place in the horizontal plane of the retractor itself. There is no capability to exert forces in the various other planes such as those substantially perpendicular to the retractor.

Other types of retractors which have been particularly adapted for use in hand surgery include a specially designed surgical table. The surgical table, like the pallet-shaped retractor described above, may include notches in its face so that fingers and the wrist can be strapped to the table. At the same time, the table will include a series of notches along its periphery so that ball and link chains can be hooked into the periphery of the retractor and then used to hold the incision, or other tissues, in the desired position.

Again, this type of surgical table does not allow the surgeon to have three-dimensional flexibility. It is only possible to exert force in the general plane of the surgical table. In addition, this type of surgical table is not sufficiently weighted in order to maintain the hand in the desired position when outside forces of even a moderate magnitude are exerted on the hand or arm.

It can be seen by the discussion of various devices which now exist in the art, that all of the retractors currently in use for extremity surgery and the like have several severe limitations. One of the limitations of all of these retractors is that they are not sufficiently weighted to immobilize the hand and arm as the surgical procedure takes place. Thus, a small amount of accidental force exerted on the hand may move it from the desired position and may cause additional damage to the hand.

An additional limitation in the existing art is the inability to move tissues or hold tissues in a three-dimensional manner and to do so with adjustable directional forces. That is, existing retractors only allow the surgeon to exert forces in the general plane of the retractor (i.e., the "horizontal" plane). If it is desirable to hold tissue up away from the plane of the retractor, this must be done by a surgical assistant or by the surgeon himself. As a result, conventional hand surgery of any complexity requires a wide range of equipment and staff such as is generally only available in the operating room or multiple hands of assistants are required which often block the surgical view or get in the way of the surgical procedure.

An additional limitation on the existing art is that it is not possible to change the plane in which force is exerted on the surgical site. That is, forces which are exerted on the surgical site. That is, forces which are exerted on a surgical area exist only in the plane of the retractor and cannot be changed during the surgical procedure as the needs of the surgical procedure demand. Currently, if it is necessary to provide lifting forces, such as to lift a nerve in a particular manner, the surgeon or an assistant must provide this force and hold the nerve at the desired location for as long as is necessary.

As a result, it is necessary to provide a human aide in order to exert forces on the hand or parts of the hand in directions other than the plane of the retractor. In addition, it will likely be necessary to have an aide immobilize the arm and/or hand of the patient while the surgery is performed. This, however, inherently results in movements of the hand and surgical site as the aide moves. It will be appreciated that even a small movement substantially increases the risk that damage may result to the delicate nerves, blood vessels, and tendons within the surgical area. Such movement can easily cause permanent damage to the patient, especially when microsurgery is required.

As a result, what is needed in the art is a retractor and methods for its use which overcome the limitations which now exist in the art and which are discussed above. It would be an advancement in the art to provide a retractor which was flexible in its use. It would be a related advancement in the art to provide a retractor which allowed the surgeon to exert forces on the hand and the surgical area in a three-dimensional manner.

It would also be an advancement in the art to provide such a retractor which was sufficiently weighted to be able to immobilize the hand during surgery. It would also be an advancement in the art to provide such a surgical retractor and methods for its use which could provide extremely delicate forces for holding blood vessels, nerves, and related structures in a desired position in three-dimensional space. Such a surgical retractor and methods for its use are disclosed and claimed herein.

BRIEF SUMMARY AND OBJECTS OF THE INVENTION

The present invention is directed to a moldable, weighted surgical retractor and methods for its use. In addition, the present invention is directed to a system which incorporates the moldable, weighted surgical retractor in connection with various types of "stays" in order to provide the exact desired force for retracting particular structural features within the surgical area.

The moldable, weighted surgical retractor of the present invention essentially comprises a flat plate. Extending outwardly from the interior body of the plate, however, are a plurality of protrusions or arms. These arms may take a variety of configurations. For example, some of the protrusions may be molded to essentially take the shape of fingers. Alternatively, the protrusions may simply be rectangular in shape. Various configurations of the device may be desirable in order to adapt the device to particular types of surgery.

Included around the periphery of the retractor are a plurality of slots. The slots may be of any size or shape, and in one preferred embodiment simply take the form of a series of narrow cuts made into the material which forms the retractor. The function of the slots is to allow the surgeon to easily insert stays into the slot and to have the stays held securely in place. The distance between the slots and the depths of the slots are designed so that the slot widths can be pinched together or pulled apart or bent slightly to better accommodate different widths of stays or allow more force to be exerted by the stays without pulling out.

Stays of various types may be used in connection with the retractor to accomplish a variety of purposes. Such stays may vary in size from the ball and link chains used in the existing art, to extremely fine sutures. In addition, stays of varying elasticity may be used to provide very fine retractive forces. The surgeon is, therefore, provided with a great deal of flexibility in the amount of force which can be exerted on various structures within the surgical area.

For example, when it is necessary to displace a delicate nerve from the surgical area, a fine suture with carefully selected elastic properties can be used to hold the nerve in the desired position. Such a suture can be anchored in the desired location by appropriately positioning the arms of the retractor. Likewise, when it is necessary to exert greater forces, such as to hold an incision open, larger more rigid stays can easily be adapted for use with the present invention and anchored appropriately.

An additional important feature of the present invention is the ability to move the protrusions or arms both within the plane of the retractor and in a plurality of planes generally perpendicular to the retractor. That is, the protrusions or arms may be lifted upwardly, may be pushed downwardly, or may be maneuvered inwardly or outwardly with respect to the interior body of the retractor. This provides the surgeon with the ability to exert forces on the surgical area in virtually all directions.

The ability to exert such forces becomes important when it is necessary to lift part of the patient's anatomy upwardly from the surgical site. For example, on some procedures on the hand it may be desirable to lift fingers upwardly in order to provide a more desirable access to the surgical area or to hold a part in a corrected position after a delicate reconstruction while other surgery is being accomplished.

Likewise, it may be necessary to lift tendons, bones, blood vessels, nerves or other structures within the hand upwardly in order to allow surgery on those structures or to move them out of the immediate surgical area. This capability is provided by the ability to move the various arms or protrusions of the retractor and the ability to anchor various types of stays to these arms. As a result of this ability to move the arms or protrusions of the retractor in a large number of three-dimensional planes, the surgeon has the ability to exert forces in a virtually infinite variety of directions even without using a surgical assistant.

An additional use for the protrusions or arms of the present invention is to hold certain parts of the patient's anatomy in place. For example, in using the retractor in hand surgery, it may be desirable to mold one or more of the arms of the retractor around the wrist of the patient in order to more fully immobilize the hand and arm during the surgical procedure. Thus, the protrusions may act essentially as straps to hold the patient's arm, wrist, or fingers in place.

An additional important feature of the retractor is that it can be made of a weighted material. For example, in one embodiment of the present invention, the entire retractor is made from a lead sheet. It will be appreciated that weighting the retractor is extremely important in adequately immobilizing the area on which surgery is performed. Particularly in the case of delicate surgery, such as surgery on the hand, it is important to prevent movement during the surgical procedure. By forming the retractor of weighted material it is more difficult for the hand to move and more difficult for accidental outside forces on the hand to significantly jar the surgical area during surgery.

It will be appreciated that various weighted materials may be used. For example, a flexible plastic with lead encased therein may form an acceptable retractor within the scope of the present invention. Other materials may include metals such as stainless steel plated onto a lead sheet. Retractors constructed in these ways would provide all of the advantages discussed above.

The present invention has a broad potential scope of use. Not only is it adaptable for use in surgery on humans, but it is also suitable for use in veterinary surgery. Indeed, the present invention is useful outside the surgical area and may be used in any setting where delicate work is being done, such as delicate mechanical assembly.

It is, therefore, a general object of the present invention to provide a retractor and methods for its use which provide the user with a high degree of flexibility.

Accordingly, it is an object of the present invention to provide a surgical retractor which is flexible in use so that the surgeon may exert forces on the surgical area in the plane of the retractor, in planes generally perpendicular to the retractor, or in any other desired plane.

It is a further object of the present invention to provide such a retractor which is weighted so as to help immobilize the patient's anatomy sufficiently to prevent movement during surgery.

It is also an object of the present invention to provide methods and apparatus for exerting a wide range of forces on the anatomy, including very delicate forces.

It is an additional object of the present invention to provide a retractor system where the retractor of the present invention can be used in connection with a wide variety of stays to provide the surgeon with additional flexibility in the use of the retractor.

These and other objects of the invention will become apparent upon reading the following detailed description and appended claims, and upon reference to the accompanying drawings.

BRIEF DESCRIPTION OF THE DRAWINGS

FIG. 1 is a top plan view of a preferred embodiment of the present invention.

FIG. 2 is a cross-sectional view of the embodiment of the invention shown in FIG. 1 along line 2—2 in FIG. 1.

DETAILED DESCRIPTION OF THE PREFERRED EMBODIMENTS

Figure 3:
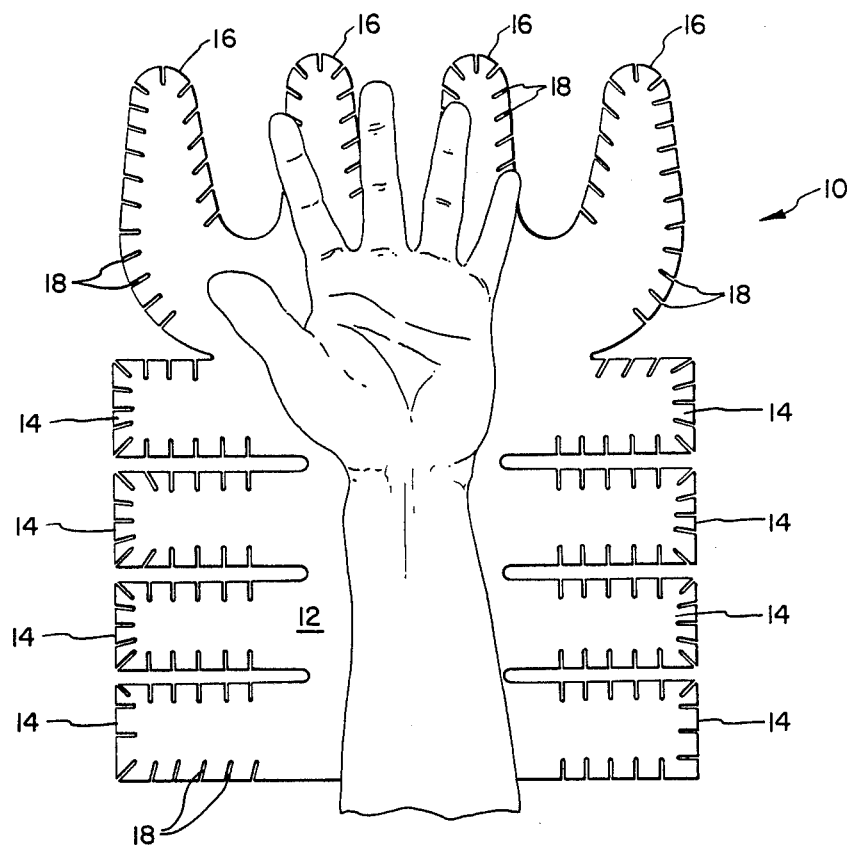
FIG. 3 is a top perspective view showing the relationship of a hand with the retractor of the present invention.

The present invention can be best understood by reference to the drawings, wherein like parts are designated with like numerals throughout. Referring more particularly to FIG. 1, one embodiment within the scope of the present invention is illustrated. As mentioned above, the present invention is related to a retractor and methods for its use in delicate surgery. In particular, the present invention is particularly adaptable for use in extremity surgery, including head and neck, and related types of surgery.

As illustrated in FIG. 1, the tractor of the present invention is generally designated 10. As can be appreciated from the drawings, the retractor 10 is generally comprised of a plate of metal or similar moldable material. The retractor 10 includes an interior body 12 of the retractor plate. Extending outwardly from the interior body 12 of the retractor plate are a plurality of protrusions or arms.

Specifically, as illustrated in FIG. 1, two types of arms or protrusions are included within the embodiment of the device illustrated. The first type of arm is essentially a rectangular arm 14. It will be appreciated that the rectangular arms 14 may take a variety of sizes and configurations as required by the expected use of the retractor 10. In particular, for some uses of the retractor 10, it may be desirable to extend certain rectangular arms 14 or to abbreviate certain of the rectangular arms 14.

Also illustrated in FIG. 1 are a plurality of curved arms 16. Again, it will be appreciated that the configuration of curved arm 16 illustrated in FIG. 1 is but one possible embodiment of the device. It may be desirable for certain procedures to vary the size and shape of the curved arm 16 to accomodate certain particular surgical procedures. However, it will be appreciated that the embodiment illustrated in FIG. 1 has been found to be extremely acceptable and desirable for use in particular types of extremity and head and neck surgery.

Also illustrated in FIG. 1 are a plurality of slots 18. As illustrated in FIG. 1, numerous slots 18 are disposed at various positions along the outside circumference of the rectangular arms 14 and curved arm 16. Again, it will be appreciated, that additional slots 18 may be disposed along the device or, indeed, fewer slots 18 or slots of a different configuration may be used in certain embodiments of the device. As will be discussed in more detail below, slots 18 are generally used in order to hold stays of various types securely in place.

The configuration of the device illustrated in FIG. 1 can be more fully appreciated with reference to FIG. 2. FIG. 2 is a cross-sectional view of the device illustrated in FIG. 1 along line 2—2 illustrated in FIG. 1.

In particular, FIG. 2 illustrates the manner in which slots 18 are disposed within the arms 14 and 16 of the retractor 10. It will be appreciated from FIG. 2 that slots 18 may be made of a variety of shapes and sizes. As a result, stays of a variety of different diameters may be held securely in place through the mechanism more fully discussed below. The particular slot arrangement illustrated has the added advantage that the metal between slots is maleable so that the slot dimensions can be increased or decreased by manual pressure.

As illustrated in FIG. 3, the retractor 10 may be formed so that it is particularly adaptable for receiving a hand or other particular part of the anatomy. In use, it is simply necessary to lay the hand or other part of the anatomy on the retractor 10 as is illustrated in FIG. 3.

Figure 4:
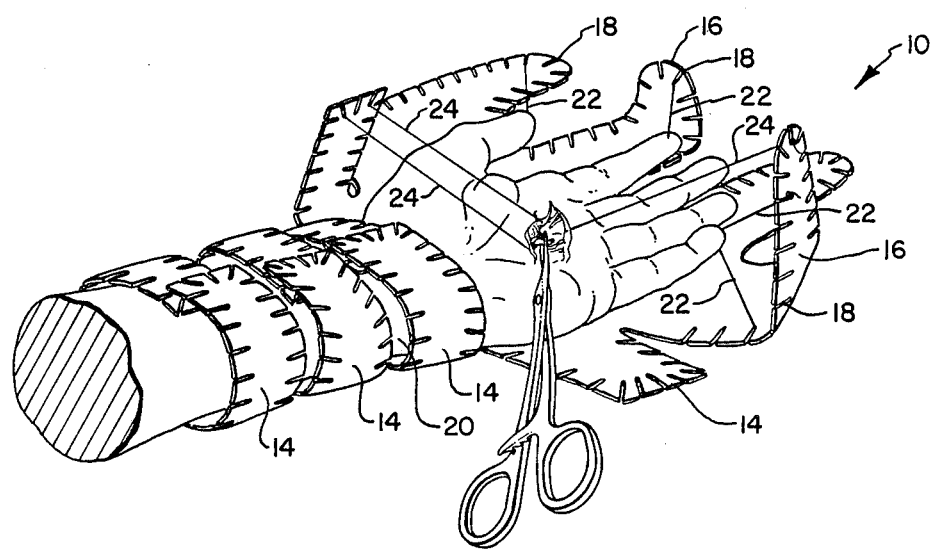
FIG. 4 is a perspective view showing the retractor of the present invention in use during hand surgery.

Once the hand is laid on the retractor 10, the hand may be immobilized as is best illustrated in FIG. 4. It is presently preferred that the retractor 10 be made of a weighted yet flexible or moldable material. One such material is lead. Other materials which may be used in constructing the retractor 10 may comprise flexible materials bonded on the outside of a lead interior.

For example, it may be desirable for some uses to electroplate stainless steel or other type of similar metal onto the exterior of the lead plate. Once the electroplating procedure is finished, the retractor 10 will still be flexible and weighted, yet a surface which may be more desirable for certain uses will be presented. Likewise, it may be desirable in certain cases to encase the lead core in a plastic material. The lead core, however, will maintain its weighted yet flexible characteristics, which characteristics will not be impeded by the plastic coating.

It will be appreciated that it is important to provide a weighted, yet moldable, material in order to fully immobilize the surgical area. The weighted material will help in holding a hand, for example, in a stable position so that the surgery can proceed. The weighted nature of the retractor 10 will also help in preventing accidental movement of the hand or extremity in the event that the surgical area is bumped or upset.

Returning to FIG. 4, the operation of the retractor 10 can be fully understood. In particular, since the retractor 10 is made from a moldable and weighted material, it is possible to position the rectangular arm 14 and curved arm 16 in any desired position without renitency.

One use of the arms 14 and 16 is to simply wrap them around a portion of the body of the individual who is the subject of the surgical procedure. As illustrated in Figure 4, this may include wrapping a plurality of the rectangular arms 14 around the wrist 20 of an individual while hand surgery is performed. Thus, the present invention allows the wrist 20 of the individual to be fully and adequately immobilized during surgery.

In addition, the flexible nature of the rectangular arms 14 allow that the mobilization can be provided at any point along the wrist 20 and, in fact, the position of rectangular arms 14 can be easily adjusted during the surgical procedure if necessary or desirable.

Furthermore, it will be appreciated that the arms 14 and 16 can be used to hold stays of various types while the surgery is proceeding. In particular, as illustrated in FIG. 4, a plurality of stays 22 may be attached directly to the patient's fingernail and then anchored into slots 18 disposed in arms 14 and 16. Stays 22 are simply a means of anchoring various fingers in the desired position during surgery. It will be appreciated that fingers could also be strapped to arms 14 and 16 if necessary or desirable.

As illustrated in FIG. 4, because of the fact that arms 14 and 16 are flexible and movable in three dimensions, stays 22 may provide forces to the fingers in a variety of directions. In particular, stays 22 as illustrated in FIG. 4 are anchored to arms 18 while arms 18 are bent into a variety of positions.

Likewise, a plurality of surgical stays 24 may also be anchored into arms 14 and 16. As illustrated in FIG. 4, surgical stays 24 run from slots in arms 14 and 16 directly to the surgical area.

Surgical stays 24 may be used to assure that the incision is maintained in the open position. Alternatively, stays 24 may be used to hold various bones, nerves, blood vessels or tendons in a particular position within the surgical area or to remove those structures from the area in which the surgeon is working.

It will be appreciated that the present invention including retractor 10 provides a substantial benefit over the existing art. In particular, arms 14 and 16 may be positioned in any particular position because of the flexible, moldable nature of retractor 10. This allows the surgeon to place stays 22 and 24 in any desired position. As a result, the surgeon is provided with the capability to provide forces in an upward direction as well as in the horizontal plane of the retractor 10. At the same time, the retractor 10 provides the surgeon with the capability of immobilizing the surgical area. Each of these functions can be performed without placing undesirable stresses on the surgical area. Thus the built-in maleability can actually prevent damage in the event that excessive unwanted motion occurs.

This three-dimensional capability of retractor 10 allows the surgeon to perform surgical procedures with decreased reliance on human assistants. For example, retractor 10 can securely hold a plurality of stays in any position desired. As a result, surgical assistants are not required to hold stays (retractors) as is the case in the conventional art. This decreased reliance on human assistants also provides more constant retraction.

In addition, the constant retraction helps assure that damage to the patient will not occur due to movement or a change in tension of the various stays during the surgical procedure. Since the stays are often attached to delicate structural features such as blood vessels and nerves, it is critical that constant retraction be provided. This has not been possible, however, in the conventional art where it is necessary to have a surgical assistant maintain the tension on a particular stay.

An additional benefit of retractor 10 is that various of the arms 14 and 16 may be wrapped around portions of the patient's anatomy in order to immobilize that portion of the anatomy. Likewise, stays 22 can be inserted within slots 18 and arms 14 and 16 in order to hold fingers or particular parts of the anatomy in a desired position and to provide further immobilization.

It will be appreciated that the retractor 10 of the present invention can be incorporated into a retractor system including both retractor 10 and various stays such as those illustrated in FIG. 4. In particular, it may be desirable to provide stays having a variety of diameters and also a variety of elastic properties.

For example, it may be desirable to provide silicon rubber stays of a very fine diameter which are capable of providing very fine forces with great elasticity when incorporated within the system. As a result, such stays could be used, for example, to hold nerve tissues and the like in a desired position. Using such fine stays would assure that such nerve tissues would not be damaged by movement of the retractor or a pulling on the stay because of the fact that the stay would readily stretch or give away.

Likewise, larger diameter latex or polyurethane stays may also be incorporated within the system of the present invention. These stiffer, larger diameter stays can be used to maintain an incision in an open position or may, indeed, may be used to hold fingers away from the surgical site such as stays 22 illustrated in FIG. 4.

For some purposes, it may be desirable to use stays of even greater strength than large diameter polyurethane or latex stays. For example, it may be necessary in certain types of surgery, such as veterinary surgery, to use the ball-and-chain stays disclosed in the prior art. It will be appreciated that such stays are readily adaptable for use with the retractor 10 in that slots 18 can be made such that they can accommodate ball-and-chain stays.

As a result, it will be appreciated that the present invention provides the surgeon with a large degree of flexibility which is not available in the prior art. For example, retractor 10 in and of itself provides a source of immobilization. That is, retractor 10 is made of a weighted material which temds to hold extremities in a desired position.

Likewise, rectangular arms 14, along with curved arms 16, may be used directly to be wrapped around, for example, the wrist or one or more fingers of the patient. Similarly, stays 22 may be attached to the fingernail or other parts of a patient and then locked securely within the arms of retractor 10 in order to hold selected fingers in position.

Retractor 10 provides a great deal of flexibility with respect to the surgical site itself. In particular, retractor 10 allows the physician to apply forces in a plurality of planes. That is, three-dimensional forces can be applied rather than simply horizontal forces as was the case in the prior art. At the same time, retractor 10 is flexible so that the direction in which forces are applied to the surgical area can be adjusted as needed during the surgical procedure. It will further be appreciated that the retractor 10 can be incorporated within a system having associated stays of varying elastic property.

In summary, the present invention accomplishes the objects set forth above. The present invention provides a surgical retractor and methods for its use which provide the surgeon with a high degree of flexibility. The surgeon is allowed to exert forces on the surgical area in the plane of the retractor in the plane perpendicular to the retractor, or in any other desired plane. The retractor is weighted so as to provide additional immobilization of the patient's anatomy during surgery. At the same time, retractor 10 is moldable so that it can further immobilize desired portions of the patient's anatomy.

Retractor 10 when associated with a variety of stays can also provide extremely delicate forces as is required in hand surgery. As a result, the need for surgical assistants is greatly reduced and surgery which conventionally requires an operating room and associated staff can now be performed in an emergency room or even in the doctor's office.

While the above discussion has focused on use of the present invention in surgery on humans the invention is also usable in other settings. For example, the present invention is suitable for use in veterinary surgery. In addition, the present invention may also be used in delicate mechanical assembly and in other non-surgical settings.

It will be appreciated that the apparatus and methods of the present invention are capable of it being incorporated in the form of a variety of embodiments, only a few of which have been ilustrated and described above. The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the range and meaning of equivalency of the claims are to be embraced within their scope.

What is claimed and desired to be secured by United States Letters Patent is:

1. A one-piece retractor for use in surgery comprising:
  a generally planar plate constructed of a material capable of flexing having an interior body portion and at least two arms extending generally outwardly from said body portion wherein said arms are constructed of a material of a thickness capable of being positioned into a plurality of positions without renitency both within the plane of the plate and in various planes above or below the plane of the plate, said planar arms having a plurality of slots disposed along their outer edges such that surgical stays may be held within said slots.

2. A one-piece retractor for use in surgery as defined in claim 1 comprising a plurality of rectangular arms.

3. A one-piece retractor for use in surgery as defined in claim 2 further comprising a plurality of curved arms.

4. A one-piece retractor for use in surgery as defined in claim 1 wherein said planar plate is made of a weighted material such that it is capable of immobilizing a portion of a patient's anatomy during surgery if securely attached to that portion of the patient's anatomy.

5. A one-piece retractor for use in surgery as defined in claim 1 wherein said planar plate and said arms are made of a moldable material.

6. A one-piece retractor for use in surgery as defined in claim 5 wherein said planar plate is made of lead integrally coated with plastic.

7. A one-piece retractor for use in surgery as defined in claim 1 wherein said planar plate is made of lead.

8. A one-piece retractor for use in surgery as defined in claim 7 wherein said planar plate is made of lead integrally coated with stainless steel.

9. A one-piece retractor for use in surgery as defined in claim 1 wherein said slots are of a plurality of sizes capable of receiving stays of a plurality of sizes.

10. A surgical retractor for use in delicate surgical procedures comprising:
 a one-piece plate lying generally in a plane and having an outside edge, said plate having an interior body portion and a plurality of arms extending generally outwardly from said body portion, said arms are constructed of a material of a thickness being capable of being placed without renitency into a plurality of positions both within the plane of the body portion and in planes both above and below the plane of the body portion;
 a plurality of slots of a plurality of sizes disposed in the outside edge of said body portion and said arms configured such that stays of a plurality of diameters can be held in place in said slots.

11. A retractor system for use in extremity surgery wherein surgery is being performed in a surgical area comprising:
 a generally planar one-piece plate lying in a particular plane and having an outside edge, said plate having an interior body portion and at least two arms extending generally outwardly from said body portion wherein said arms are constructed of a material of a thickness capable of being positioned into a plurality of positions without renitency both within the plane of the plate and in various planes above or below the plane of the plate, said planar plate and said arm having a plurality of slots disposed along its outer edge such that stays may be held within said slots; and
 a plurality of surgical stays having two ends adaptable to be secured within said slots at one end and attach to the surgical area at the other end.

12. A retractor system for use in extremity surgery as defined in claim 11 wherein said stays are of a plurality of diameters.

13. A retractor system for use in extremity surgery as defined in claim 11 wherein said stays have a plurality of elastic properties.

14. A retractor system for use in extremity surgery as defined in claim 11 comprising silicone rubber stays.

15. A retractor system for use in extremity surgery as defined in claim 11 comprising polyurethane stays.

16. A retractor system for use in extremity surgery as defined in claim 11 comprising latex stays.

17. A retractor system for use in extremity surgery as defined in claim 11 comprising ball-and-link chain stays.

18. A method of retraction for use in a surgical procedure performed on a particular portion of a patient's anatomy, said portion of the patient's anatomy comprising a surgical site, said method comprising the steps of:
 (a) providing a surgical retractor comprising a weighted plate which is capable of immobilizing a portion of a patient's anatomy during surgery, said plate lying generally in a particular plane and having an outer edge, said plate having an interior body portion and a plurality of arms extending outwardly from said body portion, said arms being constructed of a material of a thickness capable of being placed into a plurality of positions without renitency both within the plane of the body portion and in planes above and below the plane of the body portion and a plurality of slots disposed in the outside edge of said arms configured such that stays of a plurality of diameters can be held in place in said slots of a plurality of sizes;
 (b) placing the portion of the patient's anatomy which requires surgery on said surgical retractor and removably attaching the retractor to the patient by positioning the retractor arms around the patient;
 (c) removably positioning surgical stays within said slots during the surgical procedure so as to hold the surgical site in a desired position.

19. A one-piece retractor for use in surgery comprising:
 a generally planar plate having an interior body portion, a plurality of rectangular arms and a plurality of curved arms, said arms extending generally outwardly from said body portion wherein said arms are constructed of a material of a thickness capable of being positioned without renitency into a plurality of positions both within the plane of the plate and in various planes above or below the plane of the plate, said arms having a plurality of slots disposed in the outside edges of said arms such that surgical stays may be held within said slots.

20. A one-piece retractor for use in surgery as defined in claim 19 wherein said planar plate is made of a weighted material such that it is capable of immobilizing a portion of a patient's anatomy during surgery on that portion of the anatomy.

21. A one-piece flexible retractor for use in surgery as defined in claim 19 wherein said planar plate and said arm are made of a moldable material which can be placed in position without renitency.

22. A one-piece retractor for use in surgery as defined in claim 19 wherein said planar plate is made of lead.

23. A one-piece retractor for use in surgery as defined in claim 19 wherein said planar plate is made of lead coated with stainless steel.

24. A one-piece retractor for use in surgery as defined in claim 19 wherein said planar plate is made of lead coated with plastic.

25. A one-piece retractor for use in surgery as defined in claim 19 wherein said slots are of a plurality of sizes capable of receiving stays of a plurality of sizes.

* * * * *

UNITED STATES PATENT AND TRADEMARK OFFICE
CERTIFICATE OF CORRECTION

PATENT NO. : 4,798,195

DATED : January 17, 1989

INVENTOR(S) : William J. Seare, Jr.

It is certified that error appears in the above-identified patent and that said Letters Patent is hereby corrected as shown below:

Column 12, line 18, "a plurality of slots" should be --a plurality of slots of a plurality of sizes--

Signed and Sealed this

Fourteenth Day of November, 1989

Attest:

JEFFREY M. SAMUELS

Attesting Officer   Acting Commissioner of Patents and Trademarks